(12) United States Patent
Tonomura et al.

(10) Patent No.: US 10,145,744 B2
(45) Date of Patent: Dec. 4, 2018

(54) INDUCTION-HEATED ROLLER APPARATUS

(71) Applicant: TOKUDEN CO., LTD., Kyoto-shi, Kyoto (JP)

(72) Inventors: Toru Tonomura, Otsu (JP); Yasuhiro Fujimoto, Kyoto (JP); Masayoshi Kimura, Otsu (JP)

(73) Assignee: TOKUDEN CO., LTD., Kyoto-shi, Kyoto (JP)

( * ) Notice: Subject to any disclaimer, the term of this patent is extended or adjusted under 35 U.S.C. 154(b) by 491 days.

(21) Appl. No.: 14/597,201

(22) Filed: Jan. 14, 2015

(65) Prior Publication Data

US 2015/0198487 A1   Jul. 16, 2015

(30) Foreign Application Priority Data

Jan. 15, 2014 (JP) ................................. 2014-005409
May 2, 2014 (JP) ................................. 2014-095498

(51) Int. Cl.
  *G01K 13/00*  (2006.01)
  *G01B 21/10*  (2006.01)
  *G01N 27/02*  (2006.01)
  *G03G 15/20*  (2006.01)
  (Continued)

(52) U.S. Cl.
  CPC ............. *G01K 13/00* (2013.01); *G01B 21/10* (2013.01); *G01N 27/02* (2013.01);
  (Continued)

(58) Field of Classification Search
  CPC ........ G01K 13/00; G01N 27/02; G01B 21/10; G03G 15/2039; G03G 15/2053; H05B 6/06; H05B 6/145
  (Continued)

(56) References Cited

U.S. PATENT DOCUMENTS 3,686,460 A    8/1972  Lamparter et al.
6,037,576 A  * 3/2000  Okabayashi ....... G03G 15/2039
                                                            219/619

(Continued)

FOREIGN PATENT DOCUMENTS

EP       0274836 A1    7/1988
JP     S47004009 A     2/1972
(Continued)

OTHER PUBLICATIONS

European Patent Office, Extended European Search Report Issued in Application No. 15150933.8, dated Jun. 15, 2015, Germany, 5 pages.

(Continued)

*Primary Examiner* — Gregory J Toatley, Jr.
*Assistant Examiner* — Lynda Dinh
(74) *Attorney, Agent, or Firm* — Alleman Hall Creasman & Tuttle LLP

(57) ABSTRACT

The present invention intends to eliminate the need for a temperature detecting element adapted to measure the temperature of a roll main body in an induction-heated roller apparatus, and includes an impedance calculation part that calculates the impedance of a winding, a relational data storage part that stores relational data indicating the relationship between the impedance of the winding and the temperature of the roll main body, and a roll temperature calculation part that calculates the temperature of the roll main body from the impedance obtained by the impedance calculation part and the relational data stored in the relational data storage part.

6 Claims, 8 Drawing Sheets

(51) Int. Cl.
    *H05B 6/06* (2006.01)
    *H05B 6/14* (2006.01)
(52) U.S. Cl.
    CPC ..... *G03G 15/2039* (2013.01); *G03G 15/2053* (2013.01); *H05B 6/06* (2013.01); *H05B 6/145* (2013.01)
(58) Field of Classification Search
    USPC .......................................................... 702/130
    See application file for complete search history.

(56) References Cited

U.S. PATENT DOCUMENTS

| | | | |
|---|---|---|---|
| 8,457,539 B2* | 6/2013 | Nanjo | G03G 15/2064 219/619 |
| 2005/0255396 A1* | 11/2005 | Kitano | F28F 5/02 219/619 |
| 2006/0237445 A1 | 10/2006 | Nagahira et al. | |
| 2012/0145692 A1 | 6/2012 | Tabuchi | |

FOREIGN PATENT DOCUMENTS

| | | |
|---|---|---|
| JP | H11097162 A | 4/1999 |
| JP | 2001023766 A | 1/2001 |

OTHER PUBLICATIONS

Japan Patent Office, Office Action Issued in Japanese Application No. 2014-095498, dated Jan. 16, 2018, 5 pages. (Submitted with English Translation of Office Action).

\* cited by examiner

INDUCTION-HEATED ROLLER APPARATUS

TECHNICAL FIELD

The present invention relates to an induction-heated roller apparatus.

BACKGROUND ART

As disclosed in Patent Literature 1, one induction-heated roller apparatus directly measures temperature with a temperature detecting element attached to a roll main body as a heated body.

Meanwhile, a roll main body is a rotating body, and therefore in many cases, it is not easy to attach a temperature detecting element. Also, in the case of attaching a temperature detecting element to a roll main body, a contact state between the temperature detecting element and the roll main body differs individually, which may cause an error in detected temperature. Further, in order to input an output from a temperature detecting element provided in a roll main body to a fixed control device, a sophisticated device such as a rotary transformer is required.

Also, it is possible to use non-contact type temperature detecting means such as a radiation pyrometer to detect the temperature of a roll main body; however, in such a case, it is often difficult to detect an accurate temperature because detection accuracy is low or the temperature is affected by a surface radiation rate (emission rate) of the roll main body.

PRIOR TECHNICAL LITERATURES

Patent Literatures

Patent Literature 1: JP-A2001-23766

SUMMARY OF INVENTION

Technical Problem

Therefore, the present invention is made in order to solve the above-described problems, and a main intended object thereof is to eliminate the need for a temperature detecting element adapted to measure the temperature of a roll main body in an induction-heated roller apparatus.

Solution to Problem

That is, the induction-heated roller apparatus according to the present invention is an induction-heated roller apparatus including: a roll main body that is rotatably supported; a magnetic flux generating mechanism that is provided inside the roll main body and includes an iron core and a winding wound around the iron core; and a power supply circuit that is connected to the winding and provided with a control element adapted to control AC current or AC voltage. The induction-heated roller apparatus further includes: an impedance calculation part that calculates impedance of the winding from an AC current value obtained by an AC current detecting part adapted to detect AC current flowing through the winding and an AC voltage value obtained by an AC voltage detecting part adapted to detect AC voltage applied to the winding; a relational data storage part that stores relational data indicating a relationship between the impedance of the winding and temperature of the roll main body; and a roll temperature calculation part that calculates the temperature of the roll main body from the impedance obtained by the impedance calculation part and the relational data stored in the relational data storage part.

Such an apparatus includes the roll temperature calculation part that calculates the temperature of the roll main body from the impedance obtained by the impedance calculation part and the relational data indicating the relationship between the impedance of the winding and the temperature of the roll main body, and can therefore calculate the temperature of the roll main body by calculating the impedance of the winding without providing the roll main body with a temperature detecting element.

The impedance obtained by the impedance calculation part exhibits a constant variation characteristic with respect to the inner surface temperature of the roll main body as a heat generating part.

The relationship between impedance and the inner surface temperature of an examined roll main body (inside diameter Φ×surface length L) at the time of applying a rated voltage of the roll main body is given by the following approximate expression.

$$\theta_i = k_n Z^n + k_{n-1} Z^{n-1} + k_{n-2} Z^{n-2} +, \ldots, + k_2 Z^2 + k_1 Z + k_0$$

Here, $\theta_i$ is the inner surface temperature [° C.] of the roll main body, Z the impedance (=E/I), and $k_n$ (n=1, 2, ..., n) and $k_0$ factors determined by actual measured values.

In addition, there is also a predetermined relationship between the inner surface temperature of the roll main body and the surface temperature of the roll main body at normal times. For these reasons, given that the temperature difference between the inner surface temperature and surface temperature of the roll main body is θ [° C.], the roll temperature calculation part desirably corrects the temperature of the roll main body, which was obtained from the impedance and the relational data, using the temperature difference θ obtained from the following expression.

$$\theta = kP/[2\pi/\{\ln(d_2/d_1)/\lambda\}]$$

Here, $d_1$ is the inside diameter [m] of the roll main body, $d_2$ the outside diameter [m] of the roll main body, λ the thermal conductivity [W/m·° C.] of the roll main body at average temperature, and P a thermal flow rate [W/m], which has here a value obtained by dividing a calorific value [W] of the inner surface of the roll main body by a calorific inner surface length [m] (equal to a winding width). Also, k is a correction factor calculated from actual measured values.

Note that the thermal conductivity λ changes depending on a material or temperature of the roll main body, and FIG. 4 illustrates temperature-dependent thermal conductivity characteristics of, for example, carbon steel. Also, the current penetration depth of the roll main body is several pm at high frequencies of several tens of kHz to several hundred kHz, whereas at medium frequencies of 50 to 1000 Hz, a current penetration depth of several mm to several tens of mm is obtained. For example, in the case of carbon steel, the current penetration depth is approximately 10 mm at 60 Hz and 500 ° C. That is, in the case of medium frequency induction heating, the current penetration depth is deep, and therefore the difference between the temperature of the heat generating part (inner surface temperature) and the surface temperature is small as compared with that at high frequencies.

By measuring heat generation density and a temperature rise to an end point temperature under one condition, the relationship between the surface temperature of a roll main body and impedance is given by an approximate expression, and the surface temperature of the roll main body is obtained from the impedance according to the approximate function. A change in heat generation density also changes the temperature difference θ at a depth t, and a change in end point surface temperature of the roll main body changes an average temperature to change thermal conductivity as well. By calculating these values using a conversion expression, the surface temperature of the roll main body can be obtained, and therefore the surface temperature of the roll main body can be calculated from the impedance.

Desirably, inside the lateral circumferential wall of the roll main body, jacket chambers in which a gas-liquid two-phase heating medium is included are formed. The jacket chambers are ones adapted to uniform the temperature of the roll main body on the basis of heat transport through the included gas-liquid two-phase heating medium, and simultaneously uniform the surface temperature of the roll main body.

That is, detecting the temperature of the roll main body using the impedance is equivalent to detecting the average temperature of the inner surface. Accordingly, it can be said that surface temperatures of respective parts of the roll main body, which are uniformed by the jacket chambers, are equivalent to a value obtained by making necessary corrections to the temperature calculated from the impedance and converting the corrected temperature to the surface temperature.

Here, given that the cross-sectional area of the roll main body is S, the sum of cross-sectional areas of the jacket chambers is $S_j$, and the thickness of the roll main body is t, desirably, the roll temperature calculation part calculates the temperature of the roll main body with use of the temperature difference θ obtained on the assumption that the inside diameter $d_1$ of the roll main body is substituted by $d_{j1}=d_1+t\{1-\alpha(1-S_j/S)\}$, and the outside diameter $d_2$ of the roll main body is substituted by $d_{j2}=d_2-t\{1-\alpha(1-S_j/S)\}$. Note that $d_{j1}$ is a virtual inside diameter taking into account a reduction in thickness due to the jacket chambers, and $d_{j2}$ is a virtual outside diameter taking into account the reduction in thickness due to the jacket chambers.

Here, given that the cross-sectional area of the roll main body orthogonal to a rotational axis of the roll main body is S, the sum of cross-sectional areas of the jacket chambers orthogonal to the rotational axis is $S_j$, and the thickness of the roll main body is t, a thermally converted thickness $t_j$ is given by the following expression.

$$t_j = \alpha \times t(S-S_j)/S, (\alpha>1)$$

Here, α is a variable indicating a ratio of a reduction in function of the jacket chambers, which is caused by a reduction in pressure of the heating medium along with a reduction in temperature. Characteristics of the α-θ relationship are determined by the type of the heating medium and the impurity concentration in the jacket chambers.

The difference between the thickness t and the thermally converted thickness $t_j$ is given by the following expression.

$$t - t_j = t - \alpha \times t(S-S_j)/S$$
$$= t\{1 - \alpha(S-S_j)/S\}$$
$$= t\{1 - \alpha(1-S_j/S)\}$$

Accordingly, the thermally converted virtual inside diameter $d_{j1}$ and virtual outside diameter $d_{j2}$ of the roll main body are given by the following expressions.

$$d_{j1}=d_1+t\{1-\alpha(1-S_j/S)\}$$
$$d_{j2}=d_2-t\{1-\alpha(1-S_j/S)\}$$

That is, the ratio between the calculated outside and inside diameters is smaller, and therefore the temperature difference θ is also smaller. Accordingly, a temperature measurement error is also smaller.

Desirably, the induction-heated roller apparatus further includes an impedance correction part that, on the basis of a power supply voltage value obtained by a power supply voltage detecting part adapted to detect power supply voltage of the power supply circuit, corrects the impedance obtained by the impedance calculation part. In addition, desirably, the roll temperature calculation part calculates the temperature of the roll main body from corrected impedance resulting from the correction by the impedance correction part and the relational data.

A power supply voltage at the time of production shipment and when used by a user are generally different. For example, if the power supply voltage in a product specification is 200 V, the induction-heated roller apparatus is required to normally operate in the range of 190 V to 210 V. In particular, during initial temperature rising of the roll main body, input voltage is entirely applied, and therefore the impedance value should be corrected so as to correspond to a receiving voltage value.

Here, an impedance-temperature characteristics expression (the relational data) derived at the power supply voltage V1 at the time of shipment must be corrected so as to correspond to the power supply voltage V2 used by a user.

This is because of the following reason. In an equivalent circuit of a single-phase induction-heated roller (single-phase roller) illustrated in FIG. 5, when the power supply voltage changes, magnetic flux density in a magnetic circuit changes, and therefore exciting impedance $r_0$, $l_0$, and shell reactance (the reactance of the roll main body) $l_2$ change. Further, a change in shell permeability (the permeability of the roll main body) due to the change in magnetic flux density changes the current penetration depth to change shall resistance (the resistance of the roll main body) $r_2$, and thereby circuit impedance is also changed. Here, the induction-heated roller refers to a part including the roll main body and the magnetic flux generating mechanism.

In the case where the relationship between the surface temperature of the roll main body and the impedance is given by the approximate expression, the change in magnetic flux density due to the change in input voltage changes the current penetration depth, and thereby the impedance is changed. For this reason, the approximate expression should be corrected for use.

The current penetration depth a of the roll main body can be calculated from $\sigma=5.033\sqrt{(\rho/\mu s \times f)}$. In this expression, ρ is the specific resistance, μs the relative permeability, and f a frequency. Note that the relative permeability of the roll main body made of a magnetic material changes depending on magnetic flux density, and exhibits characteristics specific to a metal type. That is, by preliminarily measuring relative permeability-magnetic flux density characteristics of the magnetic material, the current penetration depth at magnetic flux density corresponding to input voltage can be calculated, and thereby the impedance inversely proportional to the current penetration depth can be corrected to determine the temperature. In addition, in the case where the material of the roll main body is, for example, carbon steel S45C, the relationship between the magnetic flux density and the relative permeability is illustrated in FIG. 7.

Further, the specific resistance also exhibits temperature-dependent variation characteristics specific to a metal type, and therefore a change in temperature changes the current penetration depth σ to change the impedance. However, an approximate expression representing the relationship between the temperature of the heat generating part of the roll main body and the impedance is an expression including a change in temperature of the heat generating part of the roll main body, and therefore not required to be corrected.

Specifically, in the case where the control element is a voltage varying device such as an induction voltage regulator, a change in input voltage to the winding as an induction coil changes the magnetic flux density of the magnetic circuit, whereas in the case where the control element is one that uses a semiconductor to control a phase angle (conduction angle) of current or voltage, a change in input voltage due to a change in conduction angle changes the magnetic flux density of the magnetic circuit, and further the temperature of the roll main body also changes to change the current penetration depth a of the roll main body.

The change in magnetic flux density due to the change in input voltage changes excitation characteristics of the magnetic circuit, and values of the exciting impedance $r_0$ and $l_0$ of the equivalent circuit in FIG. 5 also change. The excitation characteristics exhibit a relationship specific to the magnetic flux density of the magnetic circuit depending on a material of the roll main body or iron core, and therefore by preliminarily measuring the characteristics, the impedance is corrected. In addition, the relationship between the magnetic flux density and the exciting resistance caused by the magnetic flux generating mechanism in the case where the iron core of the magnetic flux generating mechanism is made of a grain-oriented silicon steel sheet having a thickness of 0.23 mm and the material of the roll main body is thermally treated carbon steel S45C is illustrated in FIG. 8.

Further, the change in magnetic flux density due to the change in input voltage also changes a value of the shell reactance $l_2$ of the equivalent circuit in FIG. 5. The shell reactance $l_2$ exhibits a variation related to the specific resistance of the roll main body and the magnetic flux density, and therefore by preliminarily measuring characteristics, the impedance is corrected. Also, reactance $l_1$ has a value determined by the structure of the roll main body, and should be calculated in advance.

Further, when the power supply voltage suddenly changes during operation of the induction-heated roller apparatus, the magnetic flux density of the magnetic circuit also suddenly changes to change the current penetration depth, and therefore the impedance changes; however, a change in temperature of the roll main body requires a considerable time lag. The time lag in temperature depends on the structure (material, size, weight, or the like) of the roll main body, and therefore it is necessary to set an individual correcting expression for each roll main body type.

In the case of a roll apparatus examined, the correcting expression is given by the following expression.

$$Z_n = \{1 - a(E - V_{in})^b\} Z_{on}$$

Here, E is a rated power supply voltage, $V_{in}$ control element input voltage, $Z_{on}$ impedance during a time interval $t_n$ before correction, n a number indicating a detection turn, and a and b roll-based constants.

For example, by substituting $Z_{on}$ calculated from an effective voltage and an effective current during a time interval $t_n$ of approximately several tens of microseconds into the above correcting expression, the corrected impedance $Z_n$ is obtained.

Further, by substituting $Z_{o(n+1)}$ obtained from an effective voltage and an effective current during the next time interval $t_{(n+1)}$ into the correcting expression, the corrected impedance $Z_{(n+1)}$ is obtained. In this manner, the impedance corrections are sequentially made for the respective time intervals.

Further, in the case where the control element is a semiconductor element, a conductance angle changes waveforms of voltage and current; however, the waveforms are respectively changed into different shapes. As a result, sharing voltage across each impedance is changed to change voltage across the exciting impedance, and thereby the magnetic flux density is changed to change the exciting impedance and the relative permeability as well. Therefore, in the case where the control element, conduction angle, and load are fixed, voltage and current each have certain shapes, and therefore a correction factor based on the conduction angle is determined.

Desirably, the induction-heated roller apparatus further includes an impedance correction part that, on the basis of the conduction angle of the control element, corrects the impedance obtained by the impedance calculation part. In addition, desirably, the roll temperature calculation part calculates the temperature of the roll main body from corrected impedance resulting from the correction by the impedance correction part and the relational data.

In the case of the examined roll main body (inside diameter Φ×surface length L) with the control element being a thyristor, a change in harmonic component due to waveform distortion changes voltages across the reactance components $l_1$ and $l_2$ in the equivalent circuit. Accordingly, the voltage applied to the exciting impedance changes to change the magnetic flux density. That is, the change in magnetic flux density changes the exciting impedance and the relative permeability, and therefore the effect of the change should be corrected.

Corrected impedance Z in which the effect of a change in phase angle of the thyristor is corrected is given by the following expression.

$$Z = a \times Z_x$$

Given $C = V/V_{in}$, $$a = a_n C^n + a_{n-1} C^{n-1} + a_{n-2} C^{n-2} + \ldots + a_2 C^2 + a_1 C^1 + a_0.$$

Here, $a_n$ is a factor that is determined for each induction-heated roller apparatus and based on actual measured values, and $a_0$ is a constant.

Also, $Z_x$ is the impedance before the correction, $V_{in}$ the receiving voltage of the thyristor, and V the output voltage of the thyristor.

Desirably, on the basis of winding temperature obtained by a temperature detecting part adapted to detect the temperature of the winding, the impedance correction part corrects the impedance obtained by the impedance calculation part.

When the temperature of the winding as a primary coil is changed by current application, $r_1$ in the equivalent circuit of the single-phase induction-heated roller (single-phase roller) illustrated in FIG. 5 changes, and therefore the circuit impedance also changes, i.e., V/I also changes. However, this change is not related to the change in temperature of the heat generating part of the roll main body, and therefore should be corrected.

The resistivity and temperature of the winding have a relationship approximately proportional to an absolute temperature, and exhibit change characteristics specific to the material of the winding. For example, in the case where the wire material is copper, the relationship is given by the following expressions, and therefore by detecting the winding temperature with a temperature sensor embedded in the winding, $r_1$ can be calculated.

$$r_1 = kL/100S [\Omega]$$

$$k = 2.1(234.5 + \theta_c)/309.5$$

Here, L is the wire length, S the wire cross-sectional area, and $\theta_c$ the winding temperature [° C.].

An induction-heated roller is generally structured such that a roll main body rotates whereas a winding as an induction coil does not rotate, and therefore embedding the temperature sensor in the winding is not difficult.

The induction-heated roller apparatus may be one including: a DC voltage application part that controls a DC power supply to intermittently apply DC voltage to the winding; and a resistance value calculation part that calculates a winding resistance value from the DC voltage applied by the DC voltage application part and DC current flowing through the winding when the DC voltage is applied, in which, on the basis of the winding resistance value obtained by the resistance value calculation part, the impedance correction part corrects the impedance obtained by the impedance calculation part.

The winding resistance value can be calculated by applying a constant DC voltage to the winding within a short period of time of several seconds and dividing the DC voltage by DC current flowing through the winding. Note that the DC voltage does not produce any inductive effect, and therefore the DC current is not affected by the roll main body or the iron core and has a relationship only with the winding resistance value. In addition, since the winding temperature does not suddenly change, even in the case of employing values periodically measured within a short period of time, a large measurement error does not occur.

Also, intermittently applying the DC voltage refers to applying the DC voltage for an application time of several seconds or less with a regular period of, for example, several seconds to several tens of minutes. Such intermittent application can reduce a biased magnetization effect produced by a DC component, and also minimally suppress an effect on an AC circuit for induction heating. Further, a winding of an induction-heated roller apparatus has generally large thermal inertia, and a change in temperature of the winding does not reach a large value during operation under a normal constant load condition. Accordingly, it can be said that performing the temperature detection, which is performed for the short application time of several seconds or less, with the period of several seconds to several tens of minutes, preferably with a period of several tens of seconds to several minutes is sufficient for temperature control of the roll main body.

Desirably, in a state where the control element provided for the power supply circuit interrupts or minimize the AC current or the AC voltage, the resistance value calculation part calculates the winding resistance value with the DC voltage being applied to the winding.

To detect only a DC component (DC current) from a current in which AC current and DC current are superimposed as a result of applying DC voltage to the winding applied with AC voltage, a complicated detection circuit is required. Note that a typical induction-heated roller apparatus includes a power supply circuit having a control element adapted to control AC current or AC voltage for controlling the temperature of a roll main body. For this reason, by using the control element to interrupt or reduce the AC current or the AC voltage to a minimum value only for the application time for applying the DC voltage, the effect of the AC current (AC component) can be suppressed to easily detect DC current (DC component). Note that the AC current or the AC voltage is interrupted or reduced to the minimum value within the short period of time of several seconds at time intervals of several seconds to several tens of minutes, which does not block an induction heating action.

One possible embodiment adapted to interrupt or reduce the AC current or the AC voltage to the minimum value, in the case where the control element is a switching device such as an electromagnetic contactor, interrupts the switching device, or in the case where the control element is a semiconductor element (power control element) such as a thyristor, minimizes a conduction phase angle of the semiconductor element.

Desirably, the roll temperature calculation part corrects the temperature of the roll main body with use of a power factor obtained by a power factor detecting part adapted to detect the power factor of an induction-heated roller including the roll main body and the magnetic flux generating mechanism; and power factor relational data indicating the relationship between the power factor of the induction-heated roller and a power factor of a reference induction-heated roller.

An induction-heated roller apparatus generally has multiple auxiliary induction-heated rollers for one control device. That is, for the one control device, interchangeability is required among the multiple auxiliary induction-heated rollers having the same specifications, and in addition, interchangeability may be required among combinations of a roll main body and a winding.

Even in the case where the induction-heated rollers have the same specifications, among the rollers, a subtle difference occurs in a finished state of a winding as an induction coil, or a subtle difference occurs in material unevenness or finished dimensions of a roll main body. Further, a difference occurs in permeability depending on an annealing state of an iron core around which a winding is wound, or an annealing state of a roll main body.

Any of the above-described differences slightly changes all of the impedances ($r_1$, $l_1$, $r_0$, $l_0$, $r_2$, and $l_2$) in the equivalent circuit of the single-phase induction-heated roller (single phase roller) illustrated in FIG. 5. As the whole of the circuit, total impedance Z changes, i.e., a resistance component R and reactance $\omega L$ of the total impedance change.

Also, the power factor is given by $\cos \varphi = R/\sqrt{\{R^2 + (\omega L)^2\}}$, and therefore along with the changes in R and L, the power factor also changes except for a singular point. Further, the impedance Z is given by $Z = \sqrt{\{R^2 + (\omega L)^2\}} = V/I$, and therefore along with the changes in R and L, V/I also changes. In addition, even in the case where the input voltage is constant, the current I and the power factor $\cos \varphi$ change, and therefore capacity P also changes. As a result, an error occurs in the surface temperature of the roll main body calculated from the reference approximate expression.

Meanwhile, in the case where the roll main body is made of a magnetic material or a composite material containing magnetic and nonmagnetic materials, and in the case where the magnetic flux density is saturated magnetic flux density or less, the power factor of the one roll main body is constant, i.e., exhibits unchanged characteristics at the temperature at which magnetism disappears, or less (in the case of carbon steel, approximately 600° C. or less) (see Table 1 below). Table 1 gives rising temperature electrical characteristics at a frequency of 60 Hz.

TABLE 1

| Temperature (° C.) | Voltage (V) | Current (A) | Capacity (kW) | Power factor | Current/Voltage |
|---|---|---|---|---|---|
| 17 | 201.0 | 198.0 | 31.34 | 0.787 | 0.985 |
| 50 | 201.9 | 184.1 | 29.31 | 0.789 | 0.912 |
| 100 | 201.0 | 167.1 | 26.53 | 0.788 | 0.831 |
| 120 | 201.4 | 163.3 | 25.93 | 0.788 | 0.811 |

It is here assumed that one induction-heated roller is used as a reference (hereinafter referred to as a reference roller), and AC voltage, AC current, power factor, and effective capacity are respectively $V_r$, $I_r$, $\cos \varphi_r$, and $P_r$. It is also assumed that AC current, power factor, and effective capacity when applying the same AC voltage $V_r$ to an induction-heated roller as a temperature detection target (hereinafter referred to as a detection target roller) are respectively $I_x$, $\cos \varphi_x$, and $P_x$.

Given that the difference in effective capacity between the detection target roller and the reference roller is $\Delta P$, the following expressions hold.

$$P_x = P_r + \Delta P$$

$$\cos \varphi_x = (P_r + \Delta P)/\{P_r/\cos \varphi_r + \Delta P/k\}$$

$$P_r + \Delta P = P_r \cdot \cos \varphi_x/\cos \varphi_r + \Delta P \cos \varphi_x/k$$

$$\Delta P(1 - \cos \varphi_x/k) = P_r(\cos \varphi_x/\cos \varphi_r - 1)$$

$$\Delta P\{(k - \cos \varphi_x)/k)\} = P_r\{(\cos \varphi_x - \cos \varphi_r)/\cos \varphi_r\}$$

$$\Delta P = \{(\cos \varphi_x - \cos \varphi_r)/\cos \varphi_r\}\{k/(k - \cos \varphi_x)\}P_r = \{k(\cos \varphi_x - \cos \varphi_r)/\cos \varphi_r(k - \cos \varphi_x)\}P_r \quad (1)$$

$$P_x = [\{k(\cos \varphi_x - \cos \varphi_r)/\cos \varphi_r(k - \cos \varphi_x)\} + 1]P_r \quad (2)$$

$$\text{Capacity ratio } P_x/P_r = \text{Expression } 2/P_r = \{k(\cos \varphi_x - \cos \varphi_r)/\cos \varphi_r(k - \cos \varphi_x)\} + 1 \quad (3)$$

The capacity ratio is equivalent to the product of a current ratio and a power factor ratio, and therefore by dividing Expression 3 by the power factor ratio, the current ratio can be obtained.

$$I_x/I_r = [\{k(\cos \varphi_x - \cos \varphi_r)/\cos \varphi_r(k - \cos \varphi_x)\} + 1]/(\cos \varphi_x/\cos \varphi_r) \quad (4)$$
$$= (k - \cos \varphi_r)/(k - \cos \varphi_x)$$

In the case of fabricating multiple induction-heated rollers, by measuring the power factor and capacity of each of the induction-heated rollers, the factor k is obtained from Expressions 3 and 4.

FIG. 6 is a characteristic graph illustrating the relationship between the surface temperature θ [° C.] of the roll main body and AC voltage/AC current (V/I), in which the thick dashed line indicates the characteristic of the reference roller, and the thick solid line indicates the characteristic of the detection target roller. Even though $\theta_x$ [° C.] of the detection target roller indicated by the thick solid line should be obtained, only $\theta_x'$ [° C.] at $V_r/I_x$ is obtained from the stored characteristic graph for the reference roller.

However, the characteristic graph for the detection target graph is not considered to be very different in characteristic from the characteristic graph for the reference roller, and therefore calculation is continued on the assumption that between the characteristic graph for the detection target roller and that for the reference roller, there is a parallel translational relationship.

First, by substituting the current $I_r = I_x(k - \cos \varphi_x)/(k - \cos \varphi_r)$ obtained from Expression 4 into the characteristic graph for the reference roller, the temperature $\theta_r$ of the reference roller at $V_r/I_r$ is calculated.

In the case of the AC current $I_x$ and the power factor $\cos \varphi_x$, the capacity of the detection target roller is changed as compared with the capacity of the reference roller by an amount corresponding to the ratio given by Expression 3, and therefore a temperature rise value also changes with the same ratio being kept.

A temperature rise value refers to the difference between the temperature of a roll main body and an ambient temperature, and given that the temperature rise value of the reference roller is $\Delta\theta_r$ [° C.], the ambient temperature in a V/I-θ characteristics approximate expression for the reference roller is $\theta_a$, and the temperature rise value of the detection target roller is $\Delta\theta_x$ [° C.], $$\Delta\theta_x = \{k(\cos \varphi_x - \cos \varphi_r)/\cos \varphi_r(k - \cos \varphi_x) + 1\}\Delta\theta_r, \quad (5)$$

and $$\theta_x = \{k(\cos \varphi_x - \cos \varphi_r)/\cos \varphi_r(k - \cos \varphi_x) + 1\}\Delta\theta_r + \theta_a. \quad (6)$$

Table 2 below gives pieces of test data obtained in the case where on the inner circumferential surface of the detection target roller (the outside diameter, inside diameter, and surface length of the roll main body are respectively 190 mm, 167 mm, and 310 mm, and made of carbon steel), a copper lining having a thickness of 0.3 mm or 0.4 mm was applied, and impedance was changed dramatically.

No. 1 roller: Without copper lining
No. 2 roller: With copper lining, copper lining thickness of 0.3 mm
No. 3 roller: With copper lining, copper lining thickness of 0.4 mm

TABLE 2

| No. | Inner circumferential copper lining | Capacity (kW) | Current (A) | Power factor |
|---|---|---|---|---|
| 1 | Without lining | 25.8 | 6.98 | 0.711 |
| 2 | 0.3 mm | 43.3 | 14.15 | 0.859 |
| 3 | 0.4 mm | 53.8 | 17.84 | 0.872 |

When obtaining the factor k in Expressions 3 and 4 from the pieces of data, k is found as:
k=1.24 for No. 1 roller and No. 2 roller,
k=1.10 for No. 1 roller and No. 3 roller, and
k=0.93 for No. 2 roller and No. 3 roller.

The pieces of data were obtained in the case where impedance was extremely changed, and between detection target rollers, there is only a slight difference. In addition, $\Delta P$ is sufficiently small as compared with $P_r$, and therefore the assumption $\Delta P \approx \Delta P/k$, i.e., k=1 is acceptable. Accordingly, Expressions 1 to 6 can be rewritten as approximate expressions as follows.

$$\Delta P = \{(\cos \varphi_x - \cos \varphi_r)/\cos \varphi_r(1 - \cos \varphi_x)\}P_r$$

$$P_x = [\{(\cos \varphi_x - \cos \varphi_r)/\cos \varphi_r(1 - \cos \varphi_x)\} + 1]P_r$$

$$P_x/P_r = \{(\cos \varphi_x - \cos \varphi_r)/\cos \varphi_r(1 - \cos \varphi_x)\} + 1$$

$$I_x/I_r = (1 - \cos \varphi_r)/(1 - \cos \varphi_x)$$

$$\Delta\theta_x = \{(\cos \varphi_x - \cos \varphi_r)/\cos \varphi_r(1 - \cos \varphi_x) + 1\}\Delta\theta_r$$

$$\theta_x = \{(\cos \varphi_x - \cos \varphi_r)/\cos \varphi_r(1 - \cos \varphi_x) + 1\}\Delta\theta_r + \theta_a$$

In the case where the number of fabricated induction-heated rollers is one, k cannot be calculated from actual measured values; however, in the case of fabricating multiple induction-heated rollers having the same specifications, by calculating the temperature from the above expressions on the assumption of k=1, an approximate value can be obtained.

ADVANTAGEOUS EFFECTS OF INVENTION

According to the present invention configured as described, without providing a roll main body with a temperature detecting element, the temperature of the roll main body can be calculated by calculating the impedance of a winding.

DESCRIPTION OF EMBODIMENTS

In the following, one embodiment of an induction-heated roller apparatus according to the present invention is described with reference to the drawings.

Figure 1:
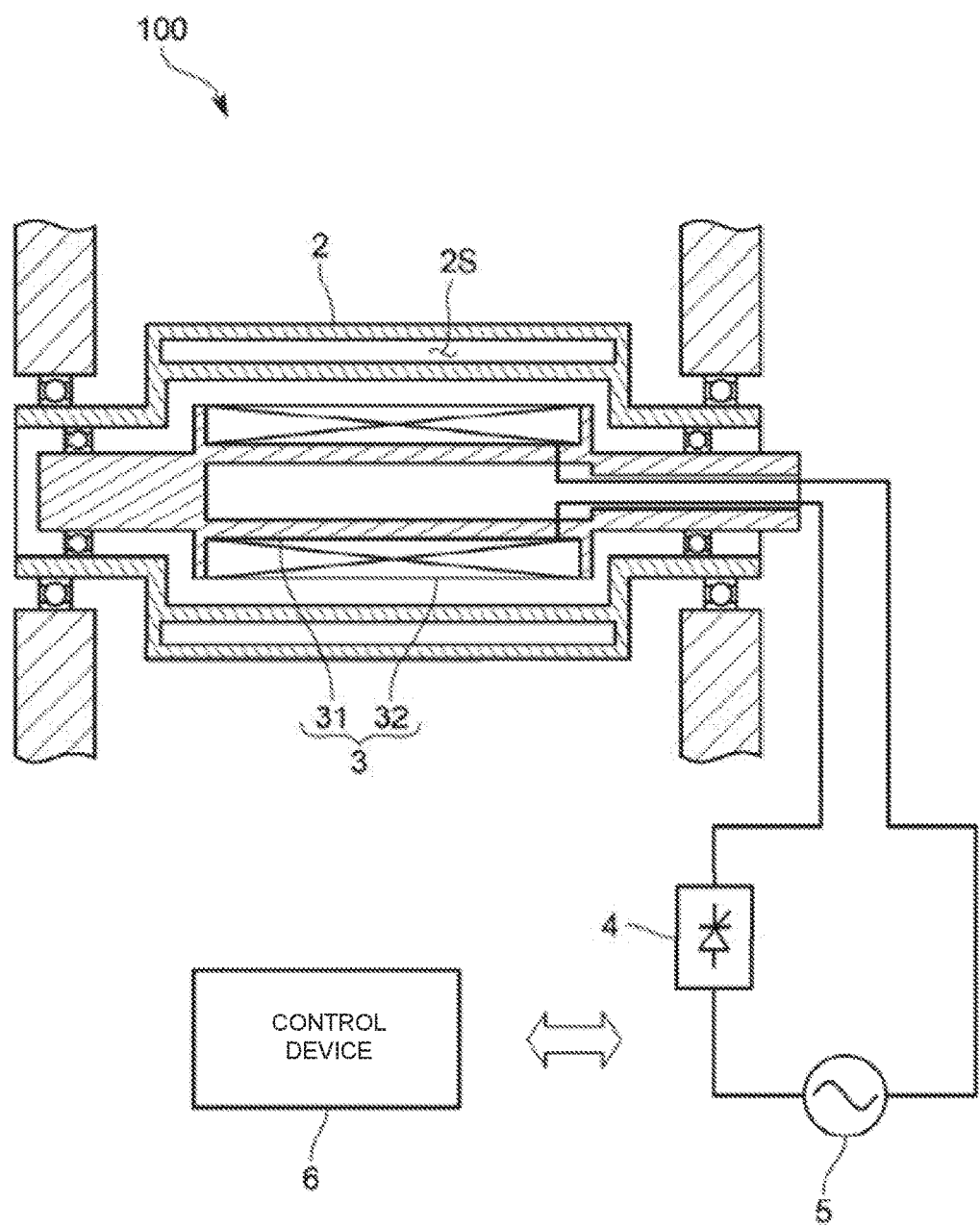
FIG. 1 is a diagram schematically illustrating a configuration of an induction-heated roller apparatus according to the present embodiment.

As illustrated in FIG. 1, an induction-heated roller apparatus 100 according to the present embodiment includes: a roll main body 2 that is rotatably supported; a magnetic flux generating mechanism 3 that is provided inside the roll main body 2 and includes an iron core 31 and a winding 32 wound around the iron core 31; and a power supply circuit 5 that is connected to the winding 32 and also provided with a control element 4 adapted to control current or voltage.

Inside the lateral circumferential wall of the roll main body 2, multiple jacket chambers 2S in which a gas-liquid two-phase heating medium is included are formed at regular intervals in a circumferential direction. In addition, the control element 4 in the present embodiment uses a semiconductor to control the conduction angle of the AC current or the AC voltage, and specifically, a thyristor.

Further, a control device 6 adapted to control the induction-heated roller apparatus 100 of the present embodiment has a surface temperature calculating function that calculates the surface temperature of the roll main body 2 from the impedance of the winding 32.

Figure 2:
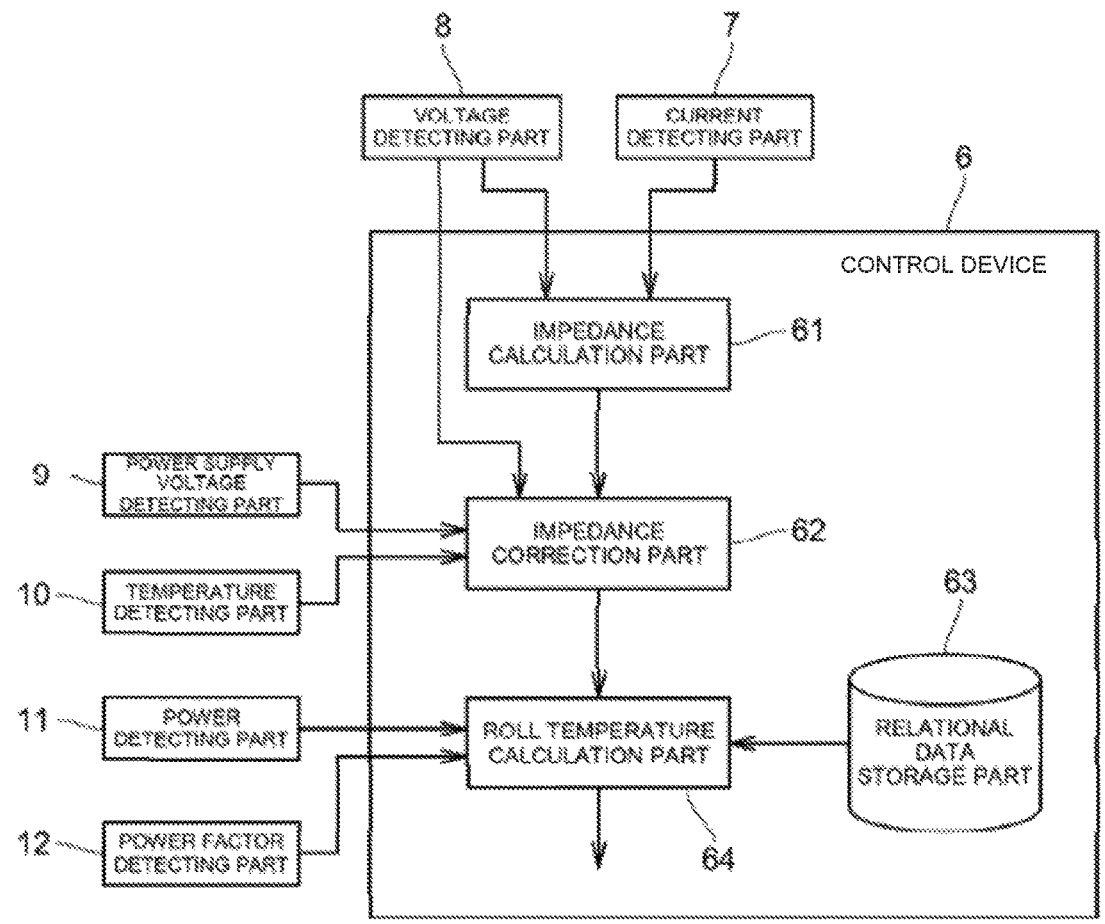
FIG. 2 is a functional configuration diagram of a control device in the same embodiment.

Specifically, the control device 6 is a dedicated or general-purpose computer including a CPU, an internal memory, an A/D converter, a D/A converter, an input/output interface, and the like. Also, the CPU and peripheral devices operate according to a predetermined program stored in the internal memory, and thereby as illustrated in FIG. 2, the control device 6 fulfills functions as an impedance calculation part 61, an impedance correction part 62, a relational data storage part 63, a roll temperature calculation part 64, and the like.

In the following, the respective parts are described with reference to a temperature calculation flowchart in FIG. 3 together with FIG. 2.

Figure 3:
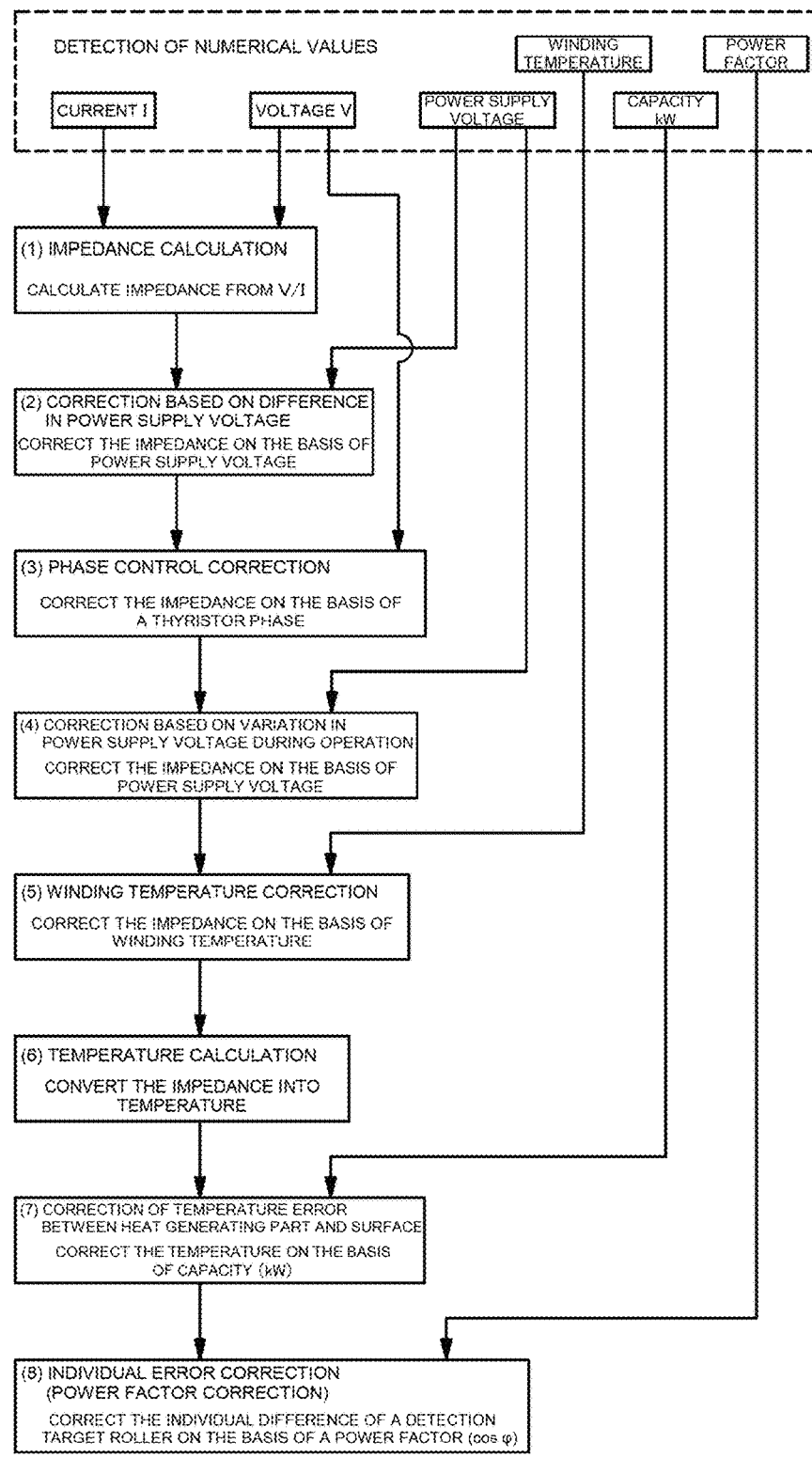
FIG. 3 is a diagram illustrating a temperature calculation flow in the same embodiment.
Figure 4:
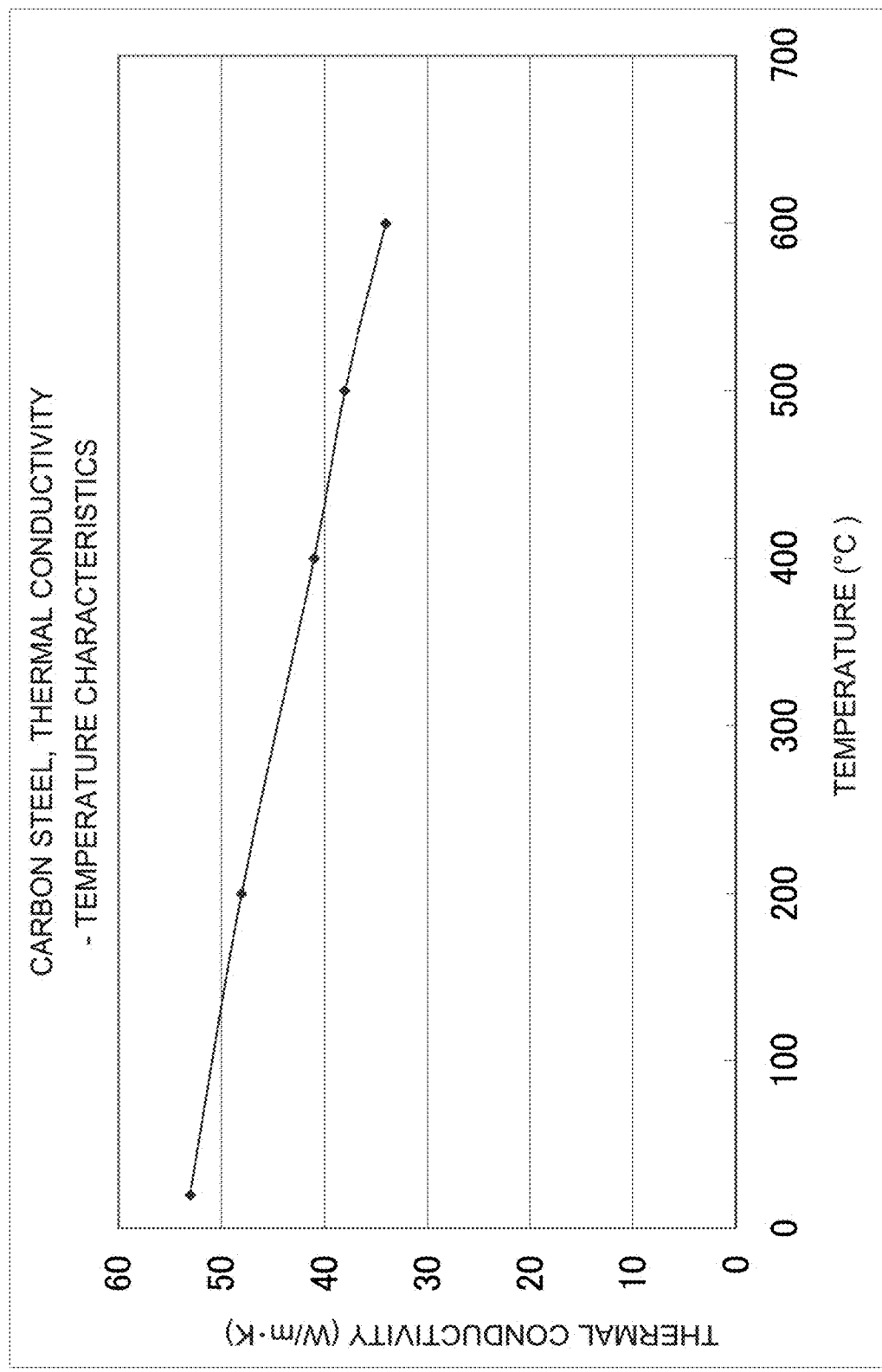
FIG. 4 is a characteristics graph illustrating the relationship between temperature and thermal conductivity of carbon steel (S45C)
Figure 5:
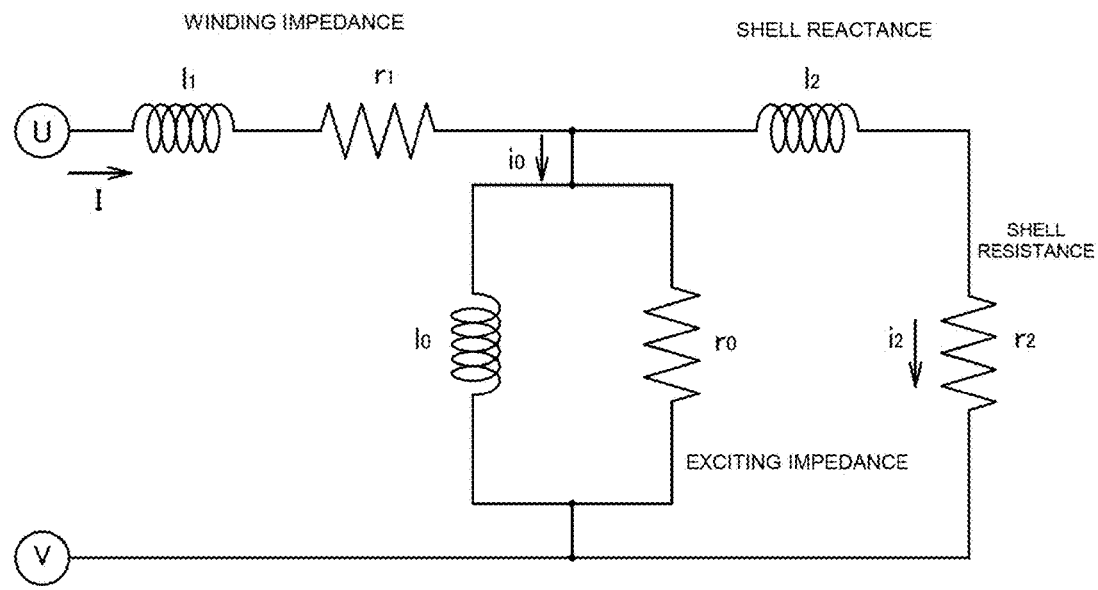
FIG. 5 is a diagram illustrating an equivalent circuit of a single-phase induction-heated roller (single-phase roller)
Figure 6:
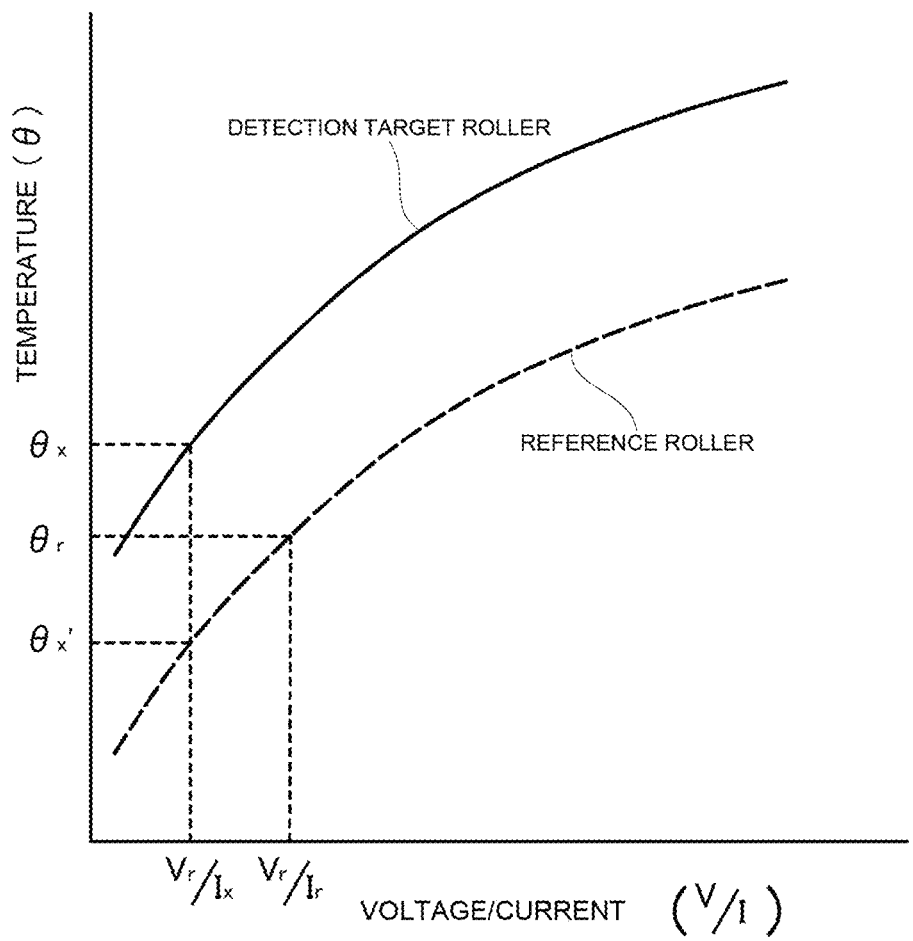
FIG. 6 is a characteristics graph illustrating the relationship between the surface temperature of a roll main body and AC voltage/AC current.
Figure 7:
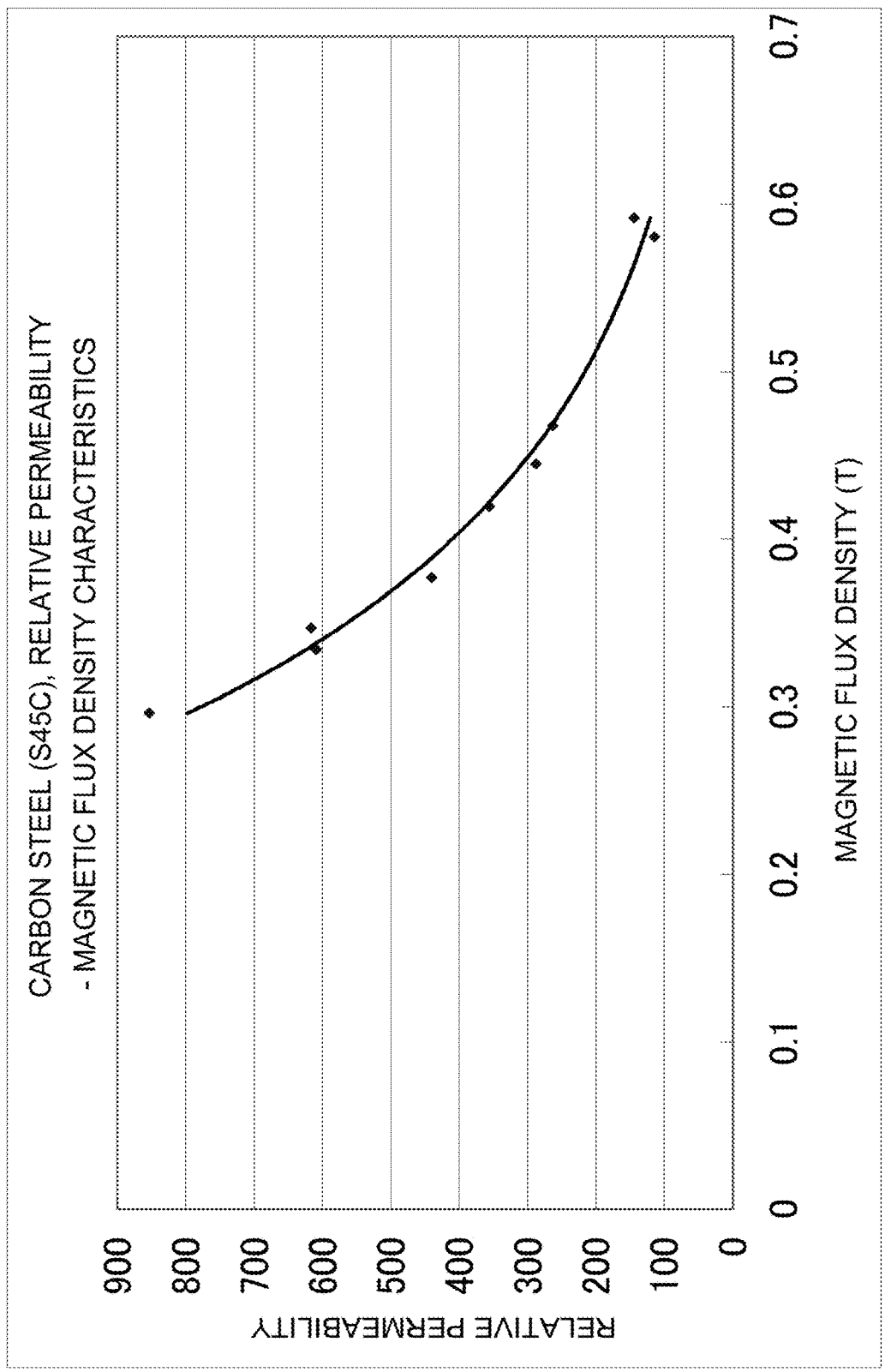
FIG. 7 is a characteristics graph illustrating the relationship between the magnetic flux density and relative permeability of carbon steel (S45C)
Figure 8:
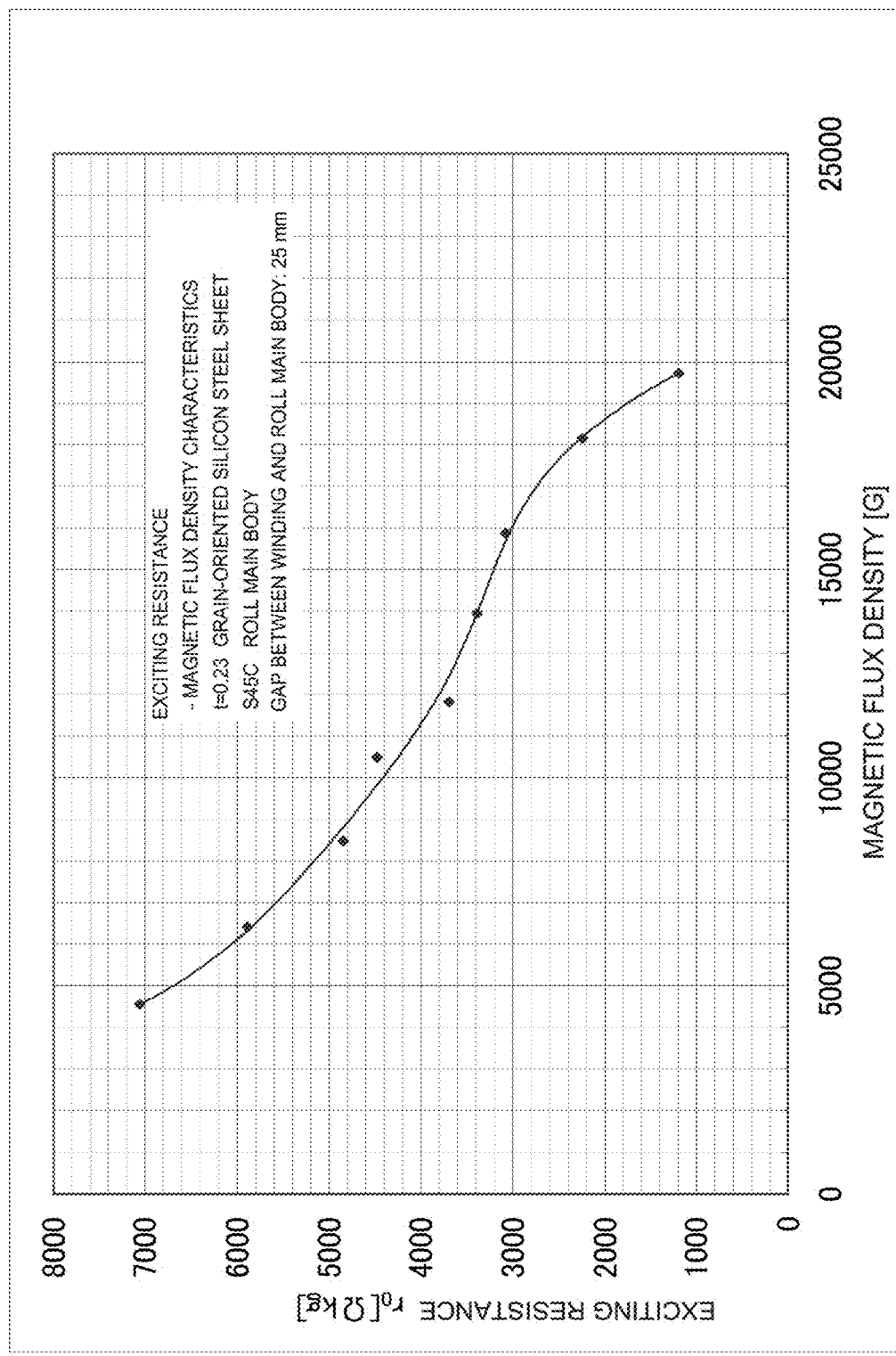
FIG. 8 is a characteristics graph illustrating the relationship between the magnetic flux density and exciting resistance of a magnetic circuit configured to include a roll main body made of carbon steel (S45C) and an iron core made of a grain-oriented silicon steel sheet.

The impedance calculation part 61 calculates the impedance $Z_1$ (=V/I) of the winding 32 from an AC current value obtained by an AC current detecting part 7 adapted to detect AC current I flowing through the winding 32 and an AC voltage value obtained by an AC voltage detecting part 8 adapted to detect AC voltage V applied to the winding 32 ((1) in FIG. 3).

The impedance correction part 62 corrects the impedance $Z_1$, which is obtained by the impedance calculation part 61, on the basis of the difference between a power supply voltage at which relational data was prepared at the time of production shipment and a power supply voltage used by a user (the difference in power supply voltage between the two) ((2) in FIG. 3).

Also, the impedance correction part 62 corrects the impedance $Z_1$ on the basis of the conduction angle (phase angle) of the control element (thyristor) 4 ((3) in FIG. 3).

Specifically, the impedance correction part 62 corrects the impedance $Z_1$ according to the following expression:

$$Z_2 = a \times Z_1$$

Here, given $C = V/V_{in}$, $$a = a_n C^n + a_{n-1} C^{n-1} + a_{n-2} C^{n-2} + \ldots + a_2 C^2 + a_1 C + a_0.$$

Here, $a_n$ is a factor that is determined for each induction-heated roller apparatus and based on measured values, and $a_0$ is a constant.

Also, $Z_1$ is the impedance before the correction, $V_{in}$ the receiving voltage of the thyristor, and V the output voltage of the thyristor.

Further, in the case where the power supply voltage suddenly changes when the induction-heated roller apparatus 100 is in operation, the magnetic flux density of a magnetic circuit also suddenly changes to change the current penetration depth of the roll main body. As a result, the impedance changes; however, a change in temperature of the roll main body requires a considerable time lag. For this reason, the impedance correction part 62 in the present embodiment corrects $Z_2$, which resulted from the correction based on the conduction angle, on the basis of a power supply voltage value E obtained by a power supply voltage detecting part 9 adapted to detect the power supply voltage of the power supply circuit 5 ((4) in FIG. 3).

Specifically, the impedance correction part 62 corrects the impedance $Z_2$ according to the following expression:

$$Z_3 = \{1 - a(E - V_{in})^b\} Z_2$$

Here, E is the rated power supply voltage, $V_{in}$ the control element input voltage, $Z_2$ the impedance before the correction, and a and b roll-based constants. This correction is continually made at separated time intervals.

Still further, the impedance correction part 62 corrects the impedance $Z_3$, which resulted from the correction based on the conduction angle and the power supply voltage E, on the basis of winding temperature $\theta_c$ [° C.] obtained by a temperature detecting part 10 adapted to detect the temperature of the winding 32 ((5) in FIG. 3). In addition, the temperature detecting part 10 is embedded in the winding 32.

Specifically, the impedance correction part 62 calculates the resistance $r_1$ of the winding 32 to correct the impedance $Z_3$ according to the following expressions.

$$r_1 = kL/100S [\Omega]$$

$$k = 2.1(234.5 + \theta_c)/309.5$$

Here, L is wire length [m], S wire cross-sectional area [mm²], and $\theta_c$ the winding temperature [° C.].

The relational data storage part 63 stores relational data indicating the relationship between the impedance of the winding 32 and the temperature of the roll main body 2 (V/I-θ characteristics approximate expression). Specifically, the relational data is data indicating the relationship between the impedance of the winding 32 and the inner surface temperature of the roll main body 2. Also, the impedance of the winding 32 was obtained by, as described above, when preliminarily obtaining the relational data, correcting the impedance, which was obtained on the basis of the AC current value obtained by the current detecting part 7 and the AC voltage value obtained by the voltage detecting part 8, on the basis of the conduction angle, power supply voltage, and winding temperature ((1) to (5) in FIG. 3). In addition, the relational data was obtained using a reference induction-heated roller apparatus. Further, the relational data storage part 63 may be set in a predetermined area of the internal memory, or set in a predetermined area of an external memory attached outside the control device 6.

The roll temperature calculation part 64 calculates the inner surface temperature of the roll main body 2 with use of: the corrected impedance resulting from the correction by the impedance correction part 62; and the relational data stored in the relational data storage part 63 ((6) in FIG. 3).

Specifically, given that the temperature difference between the inner surface temperature and surface temperature (outer surface temperature) of the roll main body 2 is θ [° C.], the roll temperature calculation part 64 calculates an accurate surface temperature by correcting the inner surface temperature using the temperature difference θ obtained from the following expression ((7) in FIG. 3).

$$\theta = kP/[2\pi/\{\ln(d_2/d_1)/\lambda\}]$$

Here, $d_1$ is the inside diameter [m] of the roll main body, $d_2$ the outside diameter [m] of the roll main body, λ the thermal conductivity [W/m·° C.] of the roll main body at an average temperature, and P a thermal flow rate [W/m], which has here a value obtained by dividing a calorific value [W] of the inner surface of the roll main body by a calorific inner surface length [m] (equal to a winding width). Also, k is a correction factor calculated from actual measured values. In addition, to obtain the thermal flow rate [W/m], the roll temperature calculation part 64 uses an electric power value obtained by a power detecting part 11.

Further, the roll temperature calculation part 64 calculates the outer surface temperature of the roll main body 2 while taking into account a reduction in thickness due to the jacket chambers 2S formed in the roll main body 2.

Specifically, on the assumption that the inside diameter $d_1$ of the roll main body 2 is substituted by a virtual inside diameter $d_{j1}$ $(=d_1+t\{1-\alpha(1-S_j/S)\})$ taking into account the reduction in thickness, and the outside diameter $d_2$ of the roll main body 2 is substituted by a virtual outside diameter $d_{j2}$ $(=d_2-t\{1-\alpha(1-S_j/S)\})$ taking into account the reduction in thickness, where S is the cross-sectional area of the roll main body 2, $S_j$ the sum of cross-sectional areas of the jacket chambers 2S, and t the thickness of the roll main body 2, the roll temperature calculation part 64 calculates the outer surface temperature of the roll main body 2 using the temperature difference θ obtained from the above expression for the temperature difference θ.

Further, the roll temperature calculation part 64 corrects an instrumental error of an induction-heated roller as a temperature detection target (detection target roller) with respect to an induction-heated roller as a reference (reference roller). Specifically, the roll temperature calculation part 64 corrects the outer surface temperature of the roll main body 2 using power factor relational data indicating the relationship between a power factor $\cos \varphi_x$ obtained by a power factor detecting part 12 adapted to detect the power factor of the detection target roller and a power factor $\cos \varphi_r$ of the reference roller ((8) in FIG. 3).

More specifically, given that a temperature rise value of the reference roller (the difference between the temperature of the roll main body and an ambient temperature) is $\Delta\theta_r$ [° C.], the ambient temperature in a V/I-θ characteristics approximate expression for the reference roller is $\theta_a$ [° C.], a temperature rise value of the detection target roller is $\Delta\theta_x$ [° C.], the power factor of the reference roller is $\cos \varphi_r$, and the power factor of the detection target roller is $\cos \varphi_x$, the roll temperature calculation part 64 calculates the surface temperature of the roll main body of the detection target roller using $\theta_x$ [° C.] obtained by the following expression.

$$\theta_x = \Delta\theta_x + \theta_a$$
$$= \{(\cos \varphi_x - \cos \varphi_r)/\cos \varphi_r(1 - \cos \varphi_x) + 1\}\Delta\theta_r + \theta_a$$

The induction-heated roller apparatus 100 of the present embodiment configured as described has the roll temperature calculation part 64 that calculates the temperature of the roll main body 2 from the impedance obtained by the impedance calculation part 61 and the relational data indicating the relationship between the impedance of the winding 32 and the temperature of the roll main body 2, and can therefore calculate the temperature of the roll main body 2 by calculating the impedance of the winding 32 without providing the roll main body 2 with a temperature detecting element.

Also, the impedance obtained by the impedance calculation part 61 is corrected by the impedance correction part 62 using the conduction angle of the thyristor 4, the power supply voltage E of the power supply circuit 5, and the temperature of the winding 32, and consequently the temperature of the roll main body 2 can be calculated with accuracy.

Further, the roll temperature calculation part 64 calculates the surface temperature on the basis of the temperature difference θ between the inner surface temperature and surface temperature of the roll main body 2, as well as correcting the instrumental error of the induction-heated roller device as a temperature detecting target with respect to the reference roller, and can therefore calculate the surface temperature of the roll main body 2 with accuracy.

Note that the present invention is not limited to the above-described embodiment.

For example, the above-described embodiment is configured such that the impedance correction part uses the temperature of the winding 32 to correct the impedance; however, the present invention may be configured such that the roll temperature calculation part 64 uses the temperature of the winding 32 to correct the temperature of the roll main body calculated from the impedance and the relational data. In this case, a correction value Δt is given by, for example, m×θ$_c$+n (where m and n are factors calculated from actual measured values).

Also, the above-described embodiment is adapted to, with reference to the approximate expression representing the predetermined relationship between the inner surface temperature of the roll main body and the impedance, correct the approximate expression to obtain the surface temperature of the roll main body. However, the present invention may be adapted to, with reference to an approximate expression representing the predetermined relationship between the surface temperature of the roll main body or the temperature inside the lateral wall of the roll main body and the impedance, on the basis of the effect of various conditions for the induction-heated roller apparatus and a variation in each of the conditions on the surface temperature, correct the approximate expression to obtain the surface temperature of the roll main body. For example, to obtain the approximate expression representing the predetermined relationship between the surface temperature of the roll main body and the impedance, it is possible to externally measure the surface temperature of the roll main body using a radiation pyrometer. Also, to correct the approximate expression, the same corrections as those in (2) to (4) and (8) in FIG. 3 in the embodiment may be made.

Further, the induction-heated roller of the above-described embodiment may be a so-called double-sided support induction-heated roller in which both end parts of a roll main body in an axial direction are rotatably supported, or a so-called single-sided support induction-heated roller in which the tubular roll main body is connected to a rotary shaft and is supported on one end of the roll only, while the unsupported end of the roll is capped.

Needless to say, the present invention is not limited to any of the above-described embodiments, but can be variously modified without departing from the scope thereof. Also needless to say, in the case where an error occurs between an actual measured value and a calculated value in each calculation step, a correction factor calculated from actual measured values is used to make a correction.

REFERENCE SIGNS LIST

100: Induction-heated roller device
2: Roll main body
2S: Jacket chamber
3: Magnetic flux generating mechanism
32: Winding
4: Control element
5: Power supply circuit
6: Control device
61: Impedance calculation part
62: Impedance correction part
63: Relational data storage part
64: Roll temperature calculation part
7: AC current detecting part
8: AC voltage detecting part
9: Power supply voltage detecting part
10: Temperature detecting part
11: Power detecting part
12: Power factor detecting part

The invention claimed is:
1. An induction-heated roller apparatus comprising:
a roll main body that is rotatably supported;
a magnetic flux generating mechanism that is provided inside the roll main body and includes an iron core and a winding wound around the iron core;
a power supply circuit that is connected to the winding of the magnetic flux generating mechanism and provided with a control element configured to control AC current or AC voltage; and
a control device operatively coupled to:
an AC current detector configured to detect AC current flowing through the winding of the magnetic flux generating mechanism to obtain an AC current value,
an AC voltage detector configured to detect AC voltage applied to the winding to obtain an AC voltage value,
a power factor detector configured to detect a power factor of the roll main body and the magnetic flux generating mechanism,
a power supply voltage detector configured to detect power supply voltage of the power supply circuit, and
a power detector configured to detect a power capacity of the roll main body, wherein the control device comprises:
a relational data storage storing relational data indicating a relationship between an impedance of the winding and an inner surface temperature of the roll main body, and
a processor executing an impedance calculation part, a roll temperature calculation part, and an impedance correction part, wherein
the impedance calculation part calculates impedance of the winding from the AC current value obtained by the AC current detector and the AC voltage value obtained by the AC voltage detector;
the roll temperature calculation part calculates the inner surface temperature of the roll main body from the impedance obtained by the impedance calculation part and the relational data stored in the relational data storage;
given that a temperature difference between the inner surface temperature and an outer surface temperature of the roll main body is θ, the roll temperature calculation part corrects the inner surface temperature of the roll main body and calculates the outer surface temperature of the roll main body with use of the temperature difference θ obtained from θ=kP/[2π/{ln(d$_2$/d$_1$)/λ}] (where d$_1$ is an inside diameter [m] of the roll main body, d$_2$ is an outside diameter [m] of the roll main body, λ is thermal conductivity [W/m·° C.] of the roll main body at average temperature, P is a thermal flow rate [W/m], and k is a correction factor calculated based on the power factor detected by the power factor detector and the power capacity detected by the power detector); and
the impedance correction part, based on a power supply voltage value obtained by the power supply voltage detector configured to detect power supply voltage of the power supply circuit, corrects the impedance obtained by the impedance calculation part; wherein the roll temperature calculation part calculates the inner surface temperature of the roll main body from corrected impedance and the relational data, without providing the roll main body with a temperature detecting element, the corrected impedance resulting from the correction by the impedance correction part.

2. The induction-heated roller apparatus according to claim 1, wherein inside a lateral circumferential wall of the roll main body, jacket chambers in which a gas-liquid two-phase heating medium is included are formed, and given that a cross-sectional area of the roll main body is S, a sum of cross-sectional areas of the jacket chambers is $S_j$, a thickness of the roll main body is t, and a variable indicating a ratio of a reduction in function of the jacket chambers is $\alpha$, the reduction being caused by a reduction in pressure of the heating medium along with a reduction in temperature, and the roll temperature calculation part calculates the outer surface temperature of the roll main body with use of the temperature difference $\theta$ obtained on an assumption that the inside diameter $d_1$ of the roll main body is substituted by $d_{j1}=d_1+t\{(1-\alpha(1-S_j/S)\}$, and the outside diameter $d_2$ of the roll main body is substituted by $d_{j2}=d_2-t\{(1-\alpha(1-S_j/S)\}$.

3. The induction-heated roller apparatus according to claim 1, wherein the control element controls a conduction angle of current or voltage with a semiconductor;

the impedance correction part, further based on the conduction angle controlled by the control element, corrects the impedance obtained by the impedance calculation part.

4. The induction-heated roller apparatus according to claim 1, wherein based on a winding temperature obtained by a temperature detector configured to detect the temperature of the winding, the impedance correction part corrects the impedance obtained by the impedance calculation part.

5. The induction-heated roller apparatus according to claim 1, wherein the processor further executes a DC voltage application part that controls a DC power supply to intermittently apply DC voltage to the winding;

the processor further executes a resistance value calculation part that calculates a winding resistance value from the DC voltage applied by the DC voltage application part and DC current flowing through the winding when the DC voltage is applied; and based on the winding resistance value obtained by the resistance value calculation part, the impedance correction part corrects the impedance obtained by the impedance calculation part.

6. The induction-heated roller apparatus according to claim 1, wherein the roll temperature calculation part corrects the outer surface temperature of the roll main body with use of:
power factor relational data indicating a relationship between the power factor of the induction-heated roller and a power factor of a reference induction-heated roller.

* * * * *